(12) United States Patent
Horn

(10) Patent No.: US 8,933,006 B1
(45) Date of Patent: *Jan. 13, 2015

(54) CONTACT LENS CLEANING COMPOSITIONS

(71) Applicant: GNT, LLC, Dana Point, CA (US)

(72) Inventor: Gerald Horn, Deerfield, IL (US)

(73) Assignee: Premium Ocular Solutions LLC., Coronado, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,237

(22) Filed: Jun. 21, 2013

(51) Int. Cl.
| | | |
|---|---|---|
| *C11D 1/722* | (2006.01) |
| *C11D 1/72* | (2006.01) |
| *C11D 1/58* | (2006.01) |
| *C11D 3/48* | (2006.01) |
| *A61L 12/14* | (2006.01) |

(52) U.S. Cl.
CPC .................................... *A61L 12/14* (2013.01)
USPC ........... 510/112; 510/421; 510/471; 510/475; 422/28

(58) Field of Classification Search
USPC ...................... 510/112, 421, 471, 475; 422/28
See application file for complete search history.

(56) References Cited

U.S. PATENT DOCUMENTS

| | | | | |
|---|---|---|---|---|
| 8,597,629 B1 * | 12/2013 | Horn | ........................... | 424/78.04 |
| 2009/0239836 A1 * | 9/2009 | Ciolkowski et al. | .......... | 514/179 |
| 2011/0105625 A1 * | 5/2011 | Nakayama et al. | ........... | 514/724 |

* cited by examiner

*Primary Examiner* — Brian P Mruk
(74) *Attorney, Agent, or Firm* — Wood, Phillips, Katz, Clark & Mortimer

(57) ABSTRACT

The invention provides a contact lens cleaning composition comprising at least two nonionic surfactants and optionally including a non-Newtonian viscosity enhancing excipient.

4 Claims, No Drawings

CONTACT LENS CLEANING COMPOSITIONS

FIELD OF THE INVENTION

The invention is directed to contact lens cleaning compositions comprising at least two nonionic surfactants and optionally comprising one or more viscosity enhancing excipients. The invention is further directed to a method of cleaning a contact lens while the contact lens remains on the eye comprising applying a contact lens cleaning compositions comprising at least two nonionic surfactants and optionally comprising one or more viscosity enhancing excipients.

BACKGROUND OF THE INVENTION

Contact lenses are worn for long periods of time each day, including those that may be worn overnight. During this time debris consisting of the macromolecular components of tears as well as particulates from the environment builds up on the surface of the lenses causing irritation to the wearer and reduced vision. Traditional methods of cleaning the debris from the surface of the contact lens includes separate steps of cleaning and rinsing, both of which requires the removal of the contact lens from the eye.

There are also multipurpose solutions that can be used for both cleaning and rinsing the contact lens. However, these multipurpose solutions tend to do a poorer job at cleaning because they must remain comfortable to the user when placed in the eye after rinsing.

There are a few products such as Alcon Opti-tears Comfort Contact Lens Drops which can be applied while the contact is on the eye. These drops moisten the contact lens and help remove debris. However, the cleaning ability of these drops does not match those of either the multipurpose or two-step solutions.

There remains a need in the art for an effective contact lens cleaning composition that can be applied while the contact remains in the eye. This cleaning composition sufficiently cleans the lens so that additional cleaning steps are not necessary and debris can be removed by the natural drainage of the eye.

SUMMARY OF THE INVENTION

In certain embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein the nonionic surfactants are selected from poloxamers, polysorbates and polyoxyl alkyls.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein the viscosity enhancing excipient is selected from carboxymethyl cellulose, carboxypropylmethyl cellulose, hydroxypropyl cellulose, hydroxyethyl cellulose, and hydroxypropylmethyl cellulose or a combination thereof.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein the nonionic surfactants are 0.10% w/v poloxamer 188, 0.20% w/v poloxamer 407 and 5.0% w/v polyoxyl 40 stearate.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein:
 the nonionic surfactants are 0.10% w/v poloxamer 188, 0.20% w/v poloxamer 407 and 5.0% w/v polyoxyl 40 stearate; and
 the viscosity enhancing agent is 0.10% w/v hydroxypropylmethyl cellulose.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein:
 the nonionic surfactants are 0.10% w/v poloxamer 188, 0.20% w/v poloxamer 407 and 5.0% w/v polyoxyl 40 stearate; and
 the viscosity enhancing agent is 0.20% w/v hydroxypropylmethyl cellulose.

In certain preferred embodiments, the present invention is directed to a contact lens cleaning composition comprising:
 1) from 0.2% to 7.0% w/v of at least two different nonionic surfactants; and
 2) from 0.0% to 1.75% w/v of a non-Newtonian viscosity enhancing excipient;
wherein:
 the nonionic surfactants are 0.10% w/v poloxamer 188, 0.20% w/v poloxamer 407 and 5.0% w/v polyoxyl 40 stearate; and
 the viscosity enhancing agent is 0.30% w/v hydroxypropylmethyl cellulose.

In certain other embodiments, the present invention is directed to a contact lens cleaning composition comprising:
 1) from 0.20% to 7.0% w/v of at least two different nonionic surfactants; and
 2) from 0.0% to 1.75% w/v hydroxypropyl cellulose.

In certain other embodiments, the present invention is directed to a contact lens cleaning composition comprising:
 1) from 0.2% to 7.0% w/v of at least two different nonionic surfactants;
 2) from 0.0% to 1.75% w/v of a non-Newtonian viscosity enhancing excipient; and
 3) from 0.1% to 1.0% w/v of glycerin.

In certain other embodiments, the present invention is directed to a method of a contact lens comprising, applying a composition comprising:
 1) from 0.2% to 7.0% w/v of at least two different nonionic surfactants; and
 2) from 0.0% to 1.75% w/v of a non-Newtonian viscosity enhancing excipient to the contact lens wherein, the contact lens remains in the eye.

DETAILED DESCRIPTION OF THE INVENTION

The present invention is directed to a contact lens cleaning composition comprising:
1) from 0.2% to 7.0% w/v of at least two different nonionic surfactants; and
2) from 0.0% to 1.75% w/v of a non-Newtonian viscosity enhancing excipient.

As used herein, the term "composition" is intended to encompass a product comprising the specified ingredients in the specified amounts, as well as any product which results, directly or indirectly, from a combination of the specified ingredients in the specified amounts.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "contact lens" refers, but is not limited to, soft contact lens for daily wear, extended wear, or unit daily disposable wear and rigid gas permeable lenses.

Nonionic surfactants that can be used in accordance with the present invention include but are not limited to poloxamers, polysorbates, cyclodextrins, and polyoxyl alkyls; where preferred embodiments include but are not limited to Poloxamer 188, Poloxamer 407, Polysorbate 20, Polysorbate 80, Polyoxyl 40 stearate, Polyoxyl 35 castor oil, and Polyoxyl 40 hydrogenated castor oil or combinations thereof.

In certain embodiments the nonionic surfactants are polysorbate 80 and polyoxyl 40 stearate.

In certain other embodiments the nonionic surfactants are poloxamer 407 and polyoxyl 40 stearate.

In certain other embodiments the nonionic surfactants are poloxamer 188, poloaxmer 407, polysorbate 80, and polyoxyl 40 stearate.

In preferred embodiments the nonionic surfactants are poloxamer 188, poloxamer 407 and polyoxyl 40 stearate.

In more preferred embodiments the amount of nonionic surfactants is 0.10% w/v poloxamer 188, 0.20% w/v poloxamer 407, and 5.0% w/v polyoxyl 40 stearate.

In other preferred embodiments the nonionic surfactants are poloxamer 188, poloxamer 407, polyoxyl 40 stearate and polyoxyl 35 castor oil.

In other embodiments the amount of polyoxyl 35 castor oil is from 0.10% to 2.5% w/v, preferably from 0.25% to 1.50% w/v including 1.00% w/v, and more preferably from 0.50% to 0.75% w/v.

In more preferred embodiments the nonionic surfactants are 0.10% w/v poloxamer 188, 0.20% w/v poloxamer 407, 5.0% w/v polyoxyl 40 stearate and 0.25% to 1.50% w/v polyoxyl 35 castor oil.

Non-Newtonian viscosity enhancing excipients that can be used in accordance with the present invention include, but are not limited to, carboxymethyl cellulose high molecular weight blend ("CMC"), methylcellulose, methyl cellulose 4000, hydroxymethyl cellulose, hydroxypropyl cellulose ("HPC"), hydroxypropylmethyl cellulose high molecular weight blend ("HPMC"), hydroxylpropyl methyl cellulose 2906, carboxypropylmethyl cellulose high molecular weight blend, hydroxyethyl cellulose, or hydroxyethyl cellulose and hyaluronic acid, such that the concentrations cumulatively do not create a phase transition to an in situ gel.

In certain embodiments CMC is present at an amount from 0.50% to 0.75% w/v including 0.50% w/v, 0.62% w/v and 0.75% w/v.

In certain embodiments HPC is present at an amount from 1.00% to 1.75% w/v including 1.00% w/v, 1.50% w/v and 1.75% w/v.

In preferred embodiments the viscosity enhancing excipient is HPMC at an amount from 0.10% to 0.50% w/v including 0.10% w/v, 0.20% w/v, 0.30% w/v, 0.40% w/v and 0.50% w/v.

In other embodiments the contact lens cleaning composition further comprises a preservative.

Preservatives that can be used in accordance with the present invention include, but are not limited to, benzalkonium chloride ("BAK"), methylparaben, polypropylparaben, chlorobutanol, thimerosal, phenylmercuric acetate, perborate, or phenylmercuric nitrate. BAK, in particular, has been found to be effective with preferred embodiments.

In more preferred embodiments the amount of BAK is 0.01% w/v.

Buffers and pH adjustors include, but are not limited to, acetate buffers, carbonate buffers, citrate buffers, phosphate buffers and borate buffers, wherein carbonate buffer is preferred. It is understood that various acids or bases can be used to adjust the pH of the composition as needed. pH adjusting agents include, but are not limited to, sodium hydroxide and hydrochloric acid. Surprisingly, pH has not been found to alter comfort in the contact lens cleaning compositions. pH of the compositions can be from 4.0 to 8.0.

In other embodiments the contact lens cleaning composition further comprises glycerin from 0.1% to 1.0% w/v, wherein 0.3% and 0.4% are preferred.

The present invention is further directed to a method of a contact lens comprising, applying a composition comprising:
1) from 0.2% to 7.0% w/v of at least two different nonionic surfactants; and
2) from 0.0% to 1.75% w/v of a non-Newtonian viscosity enhancing excipient to the contact lens wherein, the contact lens remains in the eye.

The contact lens cleaning compositions of the present invention are suitable for administration two, three or four times per day to a subject in need thereof.

Representative Embodiments

In a more preferred embodiment the contact lens cleaning composition comprises 0.10% w/v poloxamer 188, 0.20% w/v poloxamer 407, 5.0% w/v polyoxyl 40 stearate, 0.30% w/v hydroxypropylmethyl cellulose, 0.25% w/v sodium chloride and 0.01% BAK.

In a more preferred embodiment the contact lens cleaning composition comprises 0.10% w/v poloxamer 188, 0.20% w/v poloxamer 407, 5.0% w/v polyoxyl 40 stearate, 0.20% w/v hydroxypropylmethyl cellulose, 0.25% w/v sodium chloride and 0.01% BAK.

In a more preferred embodiment the contact lens cleaning composition comprises 0.10% w/v poloxamer 188, 0.20% w/v poloxamer 407, 5.0% w/v polyoxyl 40 stearate, 0.25% w/v polyoxyl 35 castor oil, 0.30% w/v hydroxypropylmethyl cellulose, 0.25% w/v sodium chloride and 0.01% BAK.

In a more preferred embodiment the contact lens cleaning composition comprises 0.10% w/v poloxamer 188, 0.20% w/v poloxamer 407, 5.0% w/v polyoxyl 40 stearate, 1.0% w/v polyoxyl 35 castor oil, 0.30% w/v hydroxypropylmethyl cellulose, 0.25% w/v sodium chloride and 0.01% BAK.

In a more preferred embodiment the contact lens cleaning composition comprises 0.10% w/v poloxamer 188, 0.20% w/v poloxamer 407, 5.0% w/v polyoxyl 40 stearate, 1.5% w/v polyoxyl 35 castor oil, 0.30% w/v hydroxypropylmethyl cellulose, 0.25% w/v sodium chloride and 0.01% BAK.

EXAMPLE

Contact lenses were worn continuously for 16 hours at which point the users complained of dry, uncomfortable lenses. Surprisingly, instillation of contact lens cleaning drops of compositions described in Table 1 provided long-lasting relief with minimal to no blurred vision upon instillation, no prolonged effect on vision and improved comfort over pre-instillation. These drops also, unexpectedly, proved durable with wetting effect lasting from 30 to 240 minutes.

those with HPMC as the non-Newtonian viscosity enhancing agent are preferred over those with CMC, HPC or combinations thereof. Of the three surfactant compositions with HPMC those that additionally include polyoxyl 35 castor oil are preferred. Compositions 12-18 are most preferred.

What is claimed is:

1. A contact lens cleaning composition comprising 0.10% w/v poloxamer 188, 0.20% w/v poloxamer 407, 5.0% w/v polyoxyl 40 stearate, 0.25% to 1.50% w/v polyoxyl 35 castor oil, 0.30% w/v hydroxypropylmethyl cellulose, 0.25% w/v sodium chloride and 0.01% w/v benzalkonium chloride.

2. The contact lens cleaning composition of claim 1, wherein polyoxyl 35 castor oil is at an amount of 0.25% w/v.

TABLE 1

Efficacy of Contact Lens Cleaning Compositions

| (% w/v) | 1 | 2 | 3 | 4 | 5 | 6 | 7 | 8 | 9 |
|---|---|---|---|---|---|---|---|---|---|
| Polyoxyl 40 stearate | 5.00% | 5.00% | 5.00% | 5.00% | 1.00% | 5.00% | 5.00% | 5.00% | 5.00% |
| Poloxamer 407 | 0.20% | 0.20% | 0.20% | 0.20% | | 0.20% | 0.20% | 0.20% | 0.20% |
| Poloxamer 188 | 0.10% | 0.10% | 0.10% | | | | 0.10% | 0.10% | 0.10% |
| Polysorbate 80 | | | | | 5.00% | | | | 1.00% |
| Polyoxyl 35 castor oil | | | | | | | | | |
| CMC | 0.75% | 0.75% | | | | | 0.50% | 0.62% | |
| HPC | | | | 1.00% | 1.50% | 1.75% | | | |
| HPMC | | 0.30% | 0.30% | | | | | | |
| Glycerin | | | 0.30% | | | | | | |
| NaCl 0.25% | ✓ | ✓ | ✓ | ✓ | ✓ | ✓ | ✓ | ✓ | ✓ |
| BAK 0.01% | ✓ | ✓ | ✓ | ✓ | ✓ | ✓ | ✓ | ✓ | ✓ |
| Visual Blur (sec) | 90 | 5 | 5 | 20 | 20 | 40 | 45 | 45 | 5 |
| Wetting Effect (min) | 30 | 30 | 60 | 60 | 60 | 60 | 90 | 30 | 60 |
| Comfort (4 is best) | 1.5 | 3.7 | 4.0 | 3.5 | 3.5 | 3.5 | 3.5 | 3.5 | 3.5 |
| Visual Quality (4 is best) | 3.0 | 3.5 | 3.5 | 3.5 | 3.5 | 3.5 | 3.5 | 3.5 | 3.5 |
| Overall Performance | 2.5 | 3.0 | 3.0 | 3.2 | 3.2 | 3.2 | 3.5 | 3.5 | 3.5 |

| (% w/v) | 10 | 11 | 12 | 13 | 14 | 15 | 16 | 17 | 18 |
|---|---|---|---|---|---|---|---|---|---|
| Polyoxyl 40 stearate | 5.00% | 5.00% | 5.00% | 5.00% | 5.00% | 5.00% | 5.00% | 5.00% | 5.00% |
| Poloxamer 407 | 0.20% | 0.20% | 0.20% | 0.20% | 0.20% | 0.20% | 0.20% | 0.20% | 0.20% |
| Poloxamer 188 | 0.10% | 0.10% | 0.10% | 0.10% | 0.10% | 0.10% | 0.10% | 0.10% | 0.10% |
| Polysorbate 80 | | | | | | | | | |
| Polyoxyl 35 castor oil | | | | | | | 0.25% | 1.00% | 1.50% |
| CMC | | | | | | | | | |
| HPC | | | | | | | | | |
| HPMC | 0.40% | 0.50% | | 0.10% | 0.20% | 0.30% | 0.30% | 0.30% | 0.30% |
| Glycerin | | | | | | | | | |
| NaCl 0.25% | √ | √ | √ | √ | √ | √ | √ | √ | √ |
| BAK 0.01% | √ | √ | √ | √ | √ | √ | √ | √ | √ |
| Visual Blur (sec) | 10 | 15 | 2 | 4 | 5 | 7 | 0 | 1 | 1 |
| Wetting Effect (min) | 60 | 60 | 30 | 45 | 60 | 60 | 120 | 240 | 240 |
| Comfort (4 is best) | 3.7 | 3.2 | 4.0 | 4.0 | 4.0 | 4.0 | 4.0 | 4.0 | 4.0 |
| Visual Quality (4 is best) | 3.7 | 3.7 | 3.7 | 3.8 | 3.9 | 3.9 | 3.9 | 4.0 | 4.0 |
| Overall Performance | 3.6 | 3.6 | 3.7 | 3.8 | 3.8 | 3.9 | 3.9 | 4.0 | 4.0 |

Contact lens cleaning compositions with three nonionic surfactants or more are preferred over those with one, or two surfactants. Polyoxyl 40 stearate>Polyoxyl 35 castor oil>Poloxamer 407>Poloxamer 188>Polysorbate 80. A cumulative concentration of nonionic surfactant of at least 5% is most preferred. Of the four surfactant compositions 3. The contact lens cleaning composition of claim 1, wherein polyoxyl 35 castor oil is at an amount of 1.00% w/v.

4. The contact lens cleaning composition of claim 1, wherein polyoxyl 35 castor oil is at an amount of 1.50% w/v.

* * * * *